United States Patent [19]
Gamble

[11] Patent Number: 5,161,530
[45] Date of Patent: Nov. 10, 1992

[54] INTERFERENTIAL THERAPY EMPLOYING SWITCHING MECHANISM

[76] Inventor: James J. Gamble, 327 Highgate Ave., Buffalo, N.Y. 14215

[21] Appl. No.: 494,428

[22] Filed: Mar. 16, 1990

[51] Int. Cl.$^5$ ............................................. A61N 1/02
[52] U.S. Cl. ............................................. 128/420 A
[58] Field of Search ...................... 128/420 A, 420 R; 606/33; 600/10, 13, 14

[56] References Cited

U.S. PATENT DOCUMENTS

| | | | |
|---|---|---|---|
| 3,096,768 | 7/1963 | Griffith, Jr. | 128/420 A |
| 4,095,602 | 6/1978 | Leveen | 128/420 A |
| 4,821,725 | 4/1989 | Azam et al. | 128/420 A |

FOREIGN PATENT DOCUMENTS 3236756 4/1984 Fed. Rep. of Germany ... 128/420 A

Primary Examiner—William E. Kamm
Assistant Examiner—Kennedy J. Schaetzle
Attorney, Agent, or Firm—James J. Ralabate

[57] ABSTRACT

This invention involves a method and device for use in an electrical stimulation treatment called interferential stimulation. Generally, conventional devices have limited treatment area capability. By use of at least one additional electrode and a switching mechanism, vastly improved area coverage can be attained. This increased coverage is possible without any substantial adverse effects to the patient being treated. The axis of each interference pattern is shifted by the switching mechanism and with the additional electrode or electrodes, provides a much more efficient and effective interferential device and method.

7 Claims, 4 Drawing Sheets

INTERFERENTIAL THERAPY EMPLOYING SWITCHING MECHANISM

This invention relates to a device and method of interferential therapy and, more particularly, to a novel system designed to expand the area exposed to the interference field pattern generated by the interferential electrical stimulation.

BACKGROUND OF THE INVENTION

There are known various methods and devices to treat pain both magnetically and electrically. Most of these methods have been used by physiotherapists and medically-trained personnel for treating pain, swelling and numerous other medical applications. Generally, these treatments involve the use of electrodes placed in contact with the body in the locality of the injury or pain sites being treated. Some of these prior art methods of therapy using electrical stimulation are disclosed in U.S. Pat. Nos. 4,117,846; 4,456,012; 4,765,310 and 4,846,181.

U.S. Pat. No. 4,117,846 (Williams) discloses a design of a disposable electrode assembly with indigitations to reduce overall cost and permit flexibility. It is suggested that in spite of the reduced surface area with the indentations, the electrode has approximately equivalent interface impedance as an electrode with continuous edges. The flexibility and free space between indentations of Williams' system also allow for greater adhesiveness between the electrode and body.

In U.S. Pat. No. 4,456,012 (Lattin) a design of an electrical device that generates both iontophoretic (direct current) and biphasic stimulation is disclosed. The circuit design allows for alternating the current type. It is indicated that this design is different as it incorporates the two current generators into one unit.

U.S. Pat. No. 4,765,310 (Deagle) is for the design of an electrode which delivers the combined and simultaneous delivery of transcutaneous electric nerve stimulation and magnetic field therapy. The disclosure of Deagle suggests that when used together the two modalities enhance each other.

In U.S. Pat. No. 4,846,181 (Miller) a technique of wound healing is defined in which high-volt direct current (galvanic) stimulation is applied with a generator that produces a rectangular-wave pulse of this type. The technique normally requires the initial treatment to have the active electrode over a wound be of negative polarity. On subsequent treatments, the active electrode is of positive polarity.

None of these prior art systems suggest the utilization of a switching device and an additional electrode in an interferential stimulation setup. By utilizing the teachings of the present invention the effective coverage is expanded substantially beyond prior art methods including that obtained by vector scan methods in current use.

Interferential therapy currently utilizes true interference of two medium frequency (over 1000 Hz) currents in the four-pole method and modulation of the intensity of a single medium frequency carrier current in the two-pole method. Both methods create intelligence waveforms or beats in the low frequency (under 1000 Hz) range using medium frequency carrier currents to be medically therapeutic. Both the two-pole and four-pole methods currently used have serious limitations.

The two-pole method permits a more specific selection of treatment location because the depth of modulation of the carrier current is 100% everywhere between the electrodes. Since the modulated current occurs even in cutaneous tissue, skin irritation may occur if current intensity is too high; see the article by M. Hogenkamp, *Interferential Therapy*, Enraf-Nonius, Holland 1983. In addition, the area of coverage is limited. The amplitude of the modulated current is diminished in areas that are not directly between the electrodes. A clinician may attempt to increase the size of the electrodes but as the edges of the two electrodes get closer together the path of least electrical resistance becomes more superficial.

The four-pole method allows for greater current intensities however there is a limitation in the area that is exposed to the effective modulated depths of the intelligence waveform. The area of the intelligence waveform is shaped like a four-petaled rosette with the axis of each petal offset to between the axes of the electrodes. Since the interference is reduced in the area where one carrier frequency current is dominant over the other carrier frequency current, the modulation depth is reduced and the treatment frequency is not effective in that region.

An attempt to overcome the limited treatment area with the four-pole method is the vector scan available on some interferential stimulators. With vector scan, the intensity of one of the carrier currents is modulated over time causing the petals of the rosette to move. This method does increase the treatment area, but the area about the electrode axes are still missed. With these limitations, diffuse areas of pain or poor electrode placement reduces the effectiveness of these three prior art methods of electrical stimulation.

The four-pole, two-pole and vector scan prior art devices and methods are all available via the Enraf Nonius Delft model Endomed 433 interferential stimulator manufactured by B. V. Enraf-Nonius, 1 Rontgenweg, P. O. Box 483, 2600 Al Delft, Holland.

SUMMARY OF THE INVENTION

It is therefore an object of this invention to provide a method of interferential therapy devoid of the above-noted disadvantages.

Another object of this invention is to provide a novel device useful in interferential electrical stimulation.

A further object of this invention is to provide a novel method of interferential electrical stimulation which expands upon the area coverage previously affected by prior art methods.

Yet a further object of this invention is to provide a system of interferential electrical stimulation that enhances the area coverage while not losing the effectiveness of the treatment rendered.

A yet still further object of this invention is to provide a system of interferential therapy that increases the region of effective stimulation using modified available equipment.

A still further object of this invention is to provide a system used in interferential therapy wherein the affected area is substantially increased without any corresponding increased irritation to the skin.

These and other objects of this invention are accomplished generally speaking by providing an interferential therapy system wherein the axes of the electrodes delivering the carrier currents (active electrodes) are shifted over a given time resulting in a substantial increase in coverage. The axes of the electrode pairs delivering the medium frequency carrier currents determine the configuration and location of the interference field (the rosette). If the axes of the electrodes delivering the carrier currents were to shift over time, the effective treatment area would also shift and be significantly increased. By introducing an additional electrode in the four-pole method (although more than one additional electrode may be used) and a switching device, the treatment area moves over time and, as a result, is less dependent on electrode placement. The switch distributes the carrier currents to the electrodes placed on the body. While we prefer to use the four-pole method, one can modify the two-pole method as described above and be within the spirit of this invention. One or more additional electrodes may be added to the two or four-pole systems determined by the desired results.

The additional electrode which is critical to this invention for use in either the two-pole or the four-pole arrangements, allows for a momentary coupling of the electrode that initially is active (about to be inactive) and the initially inactive electrode (about to become active). During the momentary coupling, the two separate electrodes, now at an equipotential state, behave as a larger single electrode. This state causes the axis of the initially singularly "active" electrode to shift to an axis between the two equipotential electrodes. Then as the switch finally decouples from the electrode that had been initially active (to make it now inactive) and to be electrically closed with the initially inactive electrode (now making it active), the axis of the electrode is now in line with the initially inactive electrode. Since the initially active electrode is now inactive, it is ready to be coupled with the next electrode (which, in the four-pole technique would be carrying the medium frequency different from the initially active electrode). This progression could continue around the entire set of electrodes to cause a progression of the interferential pattern.

The general procedure for using the method of the present invention is as follows: it involves a method for treating a patient by utilizing interferential electrical stimulation, today a two or four-pole method or system is available. This method comprises modifying these two or four-pole methods by positioning a plurality of active electrodes (connected to a source of power) on said patient's body, said plurality of electrodes comprising at least two electrodes and at least one additional electrode. This plurality of electrodes is positioned about the targeted area to be treated. The additional at least one electrode being positioned on said patient's body at a location somewhere adjacent said at least two electrodes. Means are provided for said plurality of electrodes to induce electrical tissue stimulation to thereby cause initial electrical interference patterns. Said electrical interference patterns are shifted over time to thereby continuously shift an axis of each electrode over an expanded area of said patient's body when compared to an area of said body affected by said initial electrical interference patterns. As shown in FIG. 9 and described hereinafter, each electrical interference pattern for each electrode is step-wise rotated dependent upon placement of the electrodes.

The design of the switch used in this invention is as follows: the input four channels from a conventional interferential device (such as above-noted Endomed 433) are fed by wires to a four-poled armature by way of electrical brushes. The armature feeds four ball bearing or pin electrodes arranged on a circular plate set ninety degrees from one another. These electrodes are in contact with another circular plate from which five (or more) output electrodes are fed. A more detailed description of the switch is given below in relation to FIGS. 11, 12 and 13.

When the switch is in the initial position as tested, the interference pattern is as a regular four-pole arrangement would provide. When the switch is positioned with two adjacent electrodes equipotent electrically the two electrodes behave as a single larger electrode. This causes the axes of the rosette to shift because the axes of the active electrodes are shifted. If the process is continued repeatedly, the rosette progresses much like a pinwheel spinning in a wind. Thus, as the switch advances over time, the treatment area is enlarged significantly compared to the classical four-pole method.

DESCRIPTION OF THE DRAWING AND THE PREFERRED EMBODIMENT

In order to test the electrical effects of this invention, a test set up as described hereinafter was performed.

Figure 1:
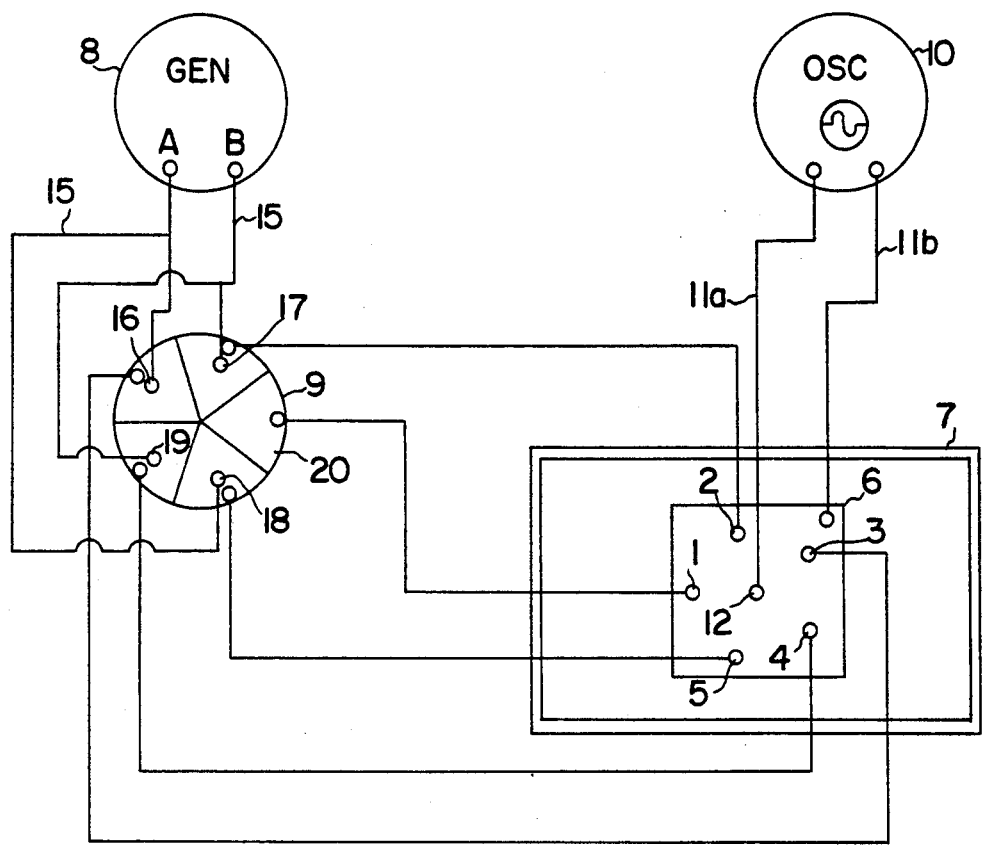
FIG. 1 is a detailed schematic illustrating the novel test set up system of this invention.

On a plexiglass sheet 6 in FIG. 1 five pin electrodes, marked 1 through 5, are set up peripherally about the treatment area. Any suitable number of electrodes varying from two or greater may be used. The plexiglass 6 is placed into a plastic pan 7 with tap water at a depth of two centimeters. An Enraf Nonius Delf model Endomed 433 interferential current generator 8 (or any other suitable interferential current generator) with circuit A set at 4000 Hz and circuit B set at 4100 Hz is used to supply medium frequency currents to a switch 9 that distributes the currents to the five electrodes 1 through 5. The generator 8 is connected to a suitable electric source. A Hewlett Packard model 130C oscilloscope 10 (or any other suitable oscilloscope) is set in ac mode to display the intelligence waveform with the neutral probe 11 placed at the center 12 of the pentagon formed by 1 through 5 and the active probe 11B movable in the conductive medium (tap water).

With each switch position, the area of modulation of greater than 50% of the carrier currents intensity is mapped using an oscilloscope 10. The location of the 50% modulated intelligence waveform, 100% modulation, and 0% modulation is mapped with each switch position using the oscilloscope 10 to measure voltage fluctuation over time.

Figure 2:
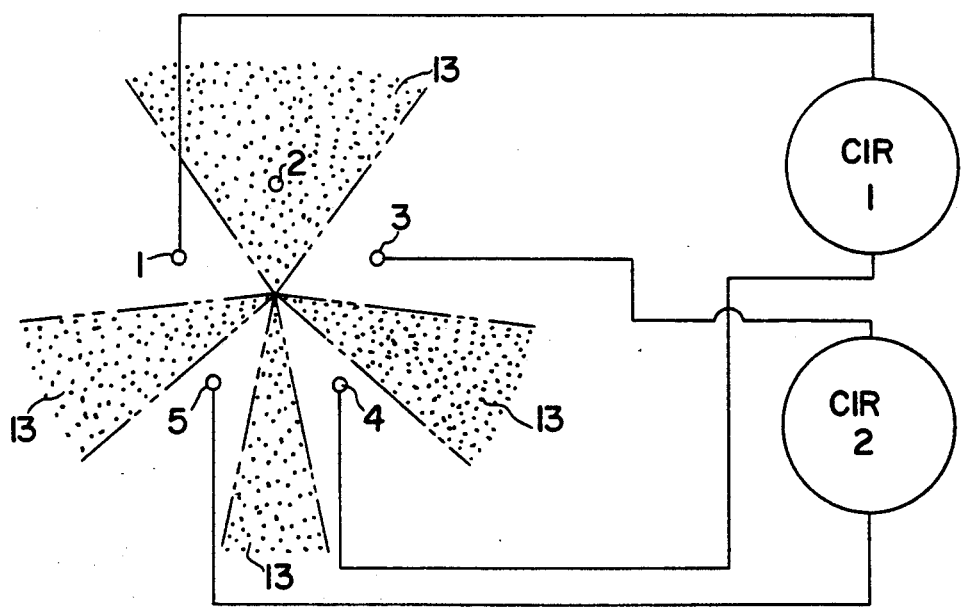
FIG. 2 illustrates the interference pattern with only four electrodes closed with the input contacts and with electrode 2 inactive.
Figure 3:
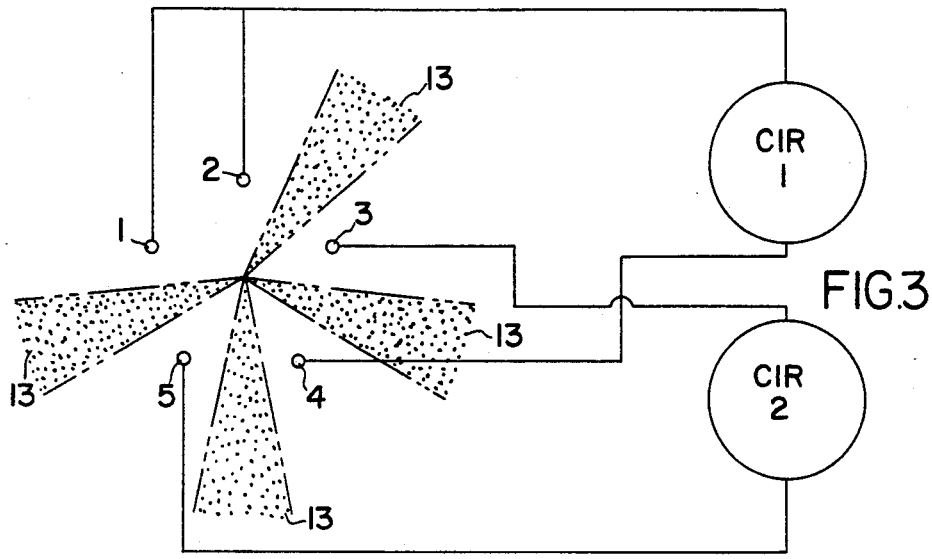
FIGS. 3–6 illustrate the interference pattern of this invention as the switch is advanced progressively.
Figure 4:
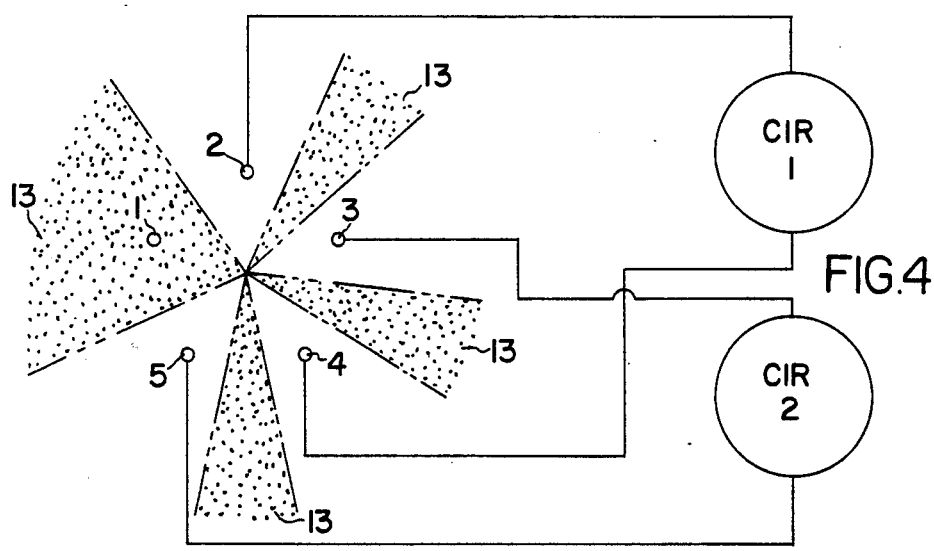
Figure 5:
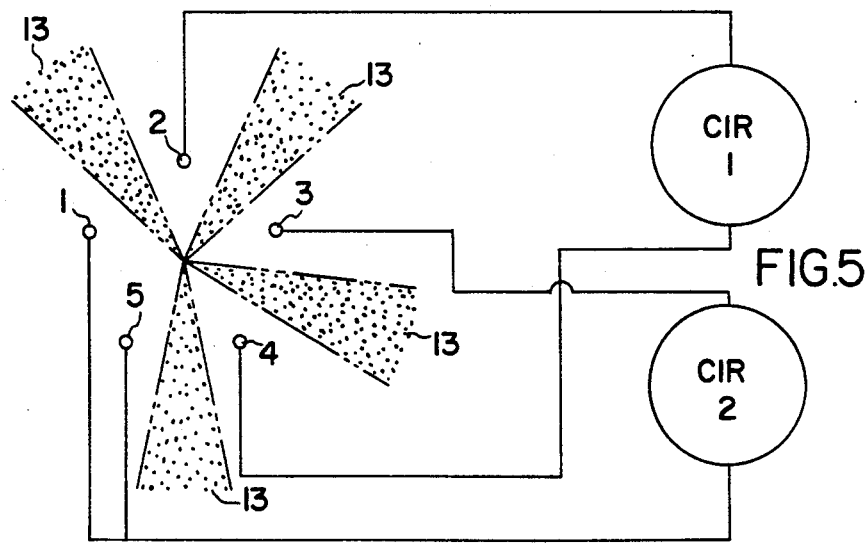
Figure 6:
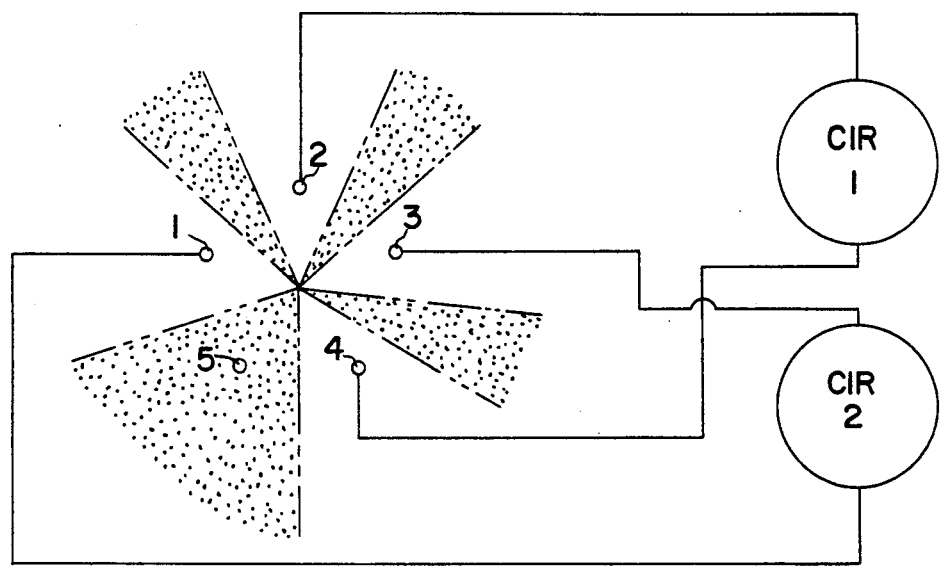

Initially, the switch 9 is in the position so that only four electrodes are closed with the input contacts as shown in FIG. 2. The switch 9 then advances so that the previously non-active electrode is equipotential with one of the adjacent electrodes as shown in FIG. 3. The switch 9 then advances further so that the initially non-active electrode is closed singularly with an input contact and the electrode which was equipotent with that electrode is now zero with respect to ground as shown in FIG. 4. The process is continued repeatedly until the initial switch position is reached.

Figure 10:
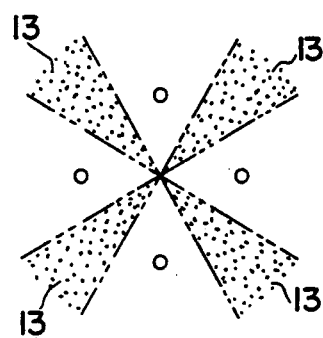
FIG. 10 illustrates the area of coverage with 50% or greater modulation formed in a conventional four-pole method of the prior art.

The maps formed from oscilloscope 10 are then compared to that of a standard prior art four-pole set-up (as shown in FIG. 10) to determine the difference between the prior art method and the method of this invention.

Figure 9:
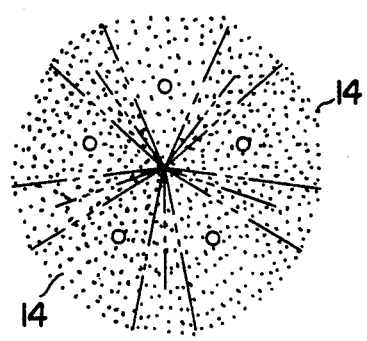
FIG. 9 illustrates the area of coverage with 50% or greater modulation formed by the system of this invention.

When the switch 9 is in the initial position, the interference pattern is as a conventional four-pole arrangement has done (FIG. 2). With the switch with two adjacent electrodes equipotential the two electrodes behave as a single larger electrode (FIG. 3). This causes the axes of the rosette 13 to shift because the axes of the active electrodes is shifted. If the process is continued repeatedly, the rosette 13 progresses much like a pinwheel spinning in a breeze (FIGS. 2-6). Thus, as the switch 9 advances over time, the treatment area as shown by the pinwheel 14 of FIG. 9 is enlarged compared to the classical four-pole method as shown in FIG. 10.

The design of the before-mentioned switch 9 is as follows: The input four channels from a conventional interferential device as 8 are fed by wires 15 to a four-poled armature by way of electrical brushes (not shown in drawing). The armature feeds four ball bearing or pin electrodes 16-19 arranged on a circular plate 20 set ninety degrees from one another. These electrodes are in contact with another circular plate in which five (or more) output electrodes are fed. Any suitable switching device inclusive of a computer chip can be used. A typical switching device used in the present invention was made as discussed below in relation to fixtures 11 and 12.

Figure 7:
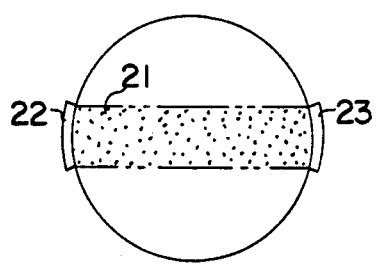
FIG. 7 illustrates the interference pattern on a conventional two-pole device of the prior art using relatively small electrodes.
Figure 8:
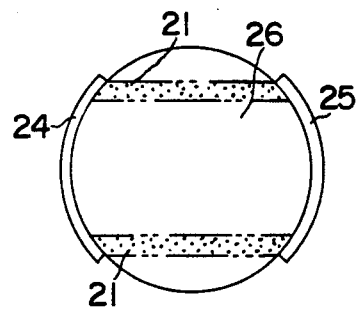
FIG. 8 illustrates the interference pattern on a conventional two-pole device of the prior art using larger electrodes.
Figure 11:
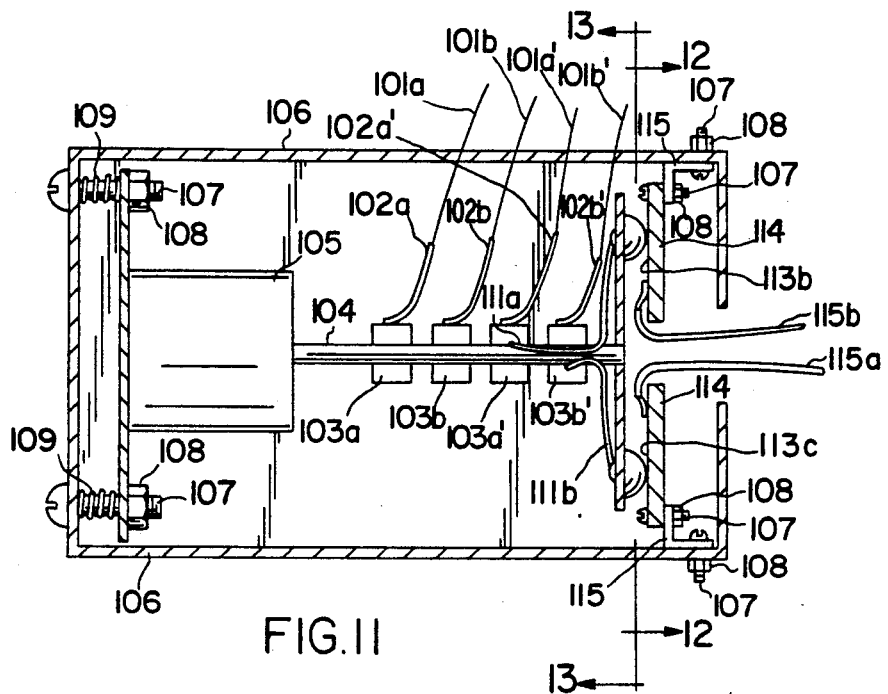
FIG. 11 is a side view schematic illustration of the switch used in the present invention.
Figure 12:
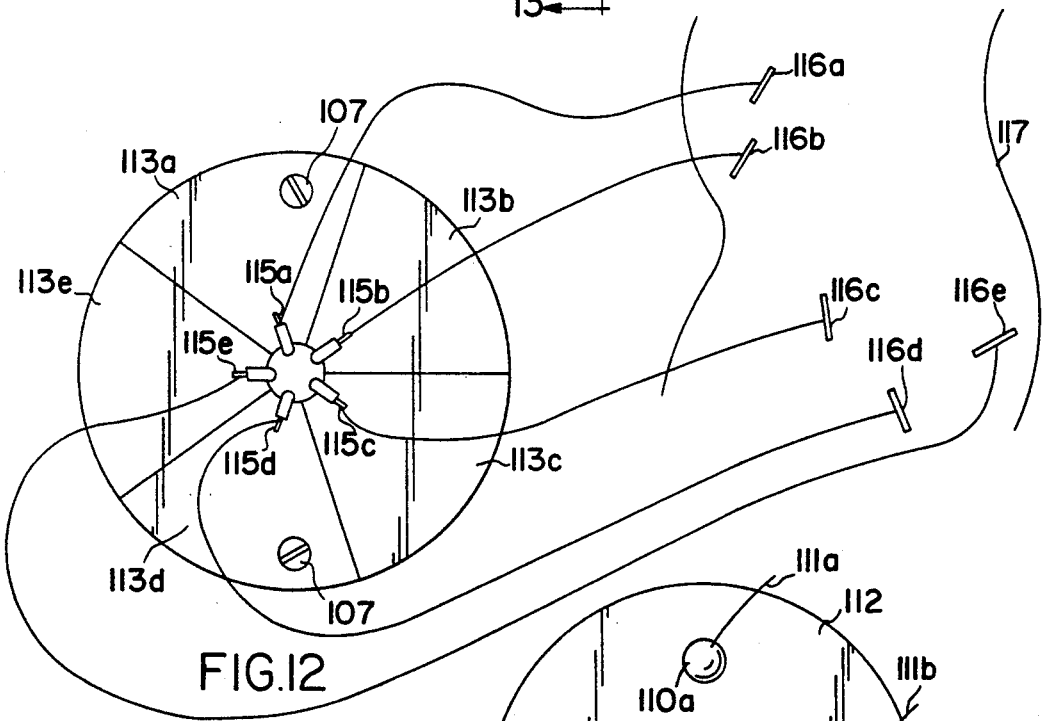
FIG. 12 is a front view schematic illustrating the switch used in the present invention.
Figure 13:
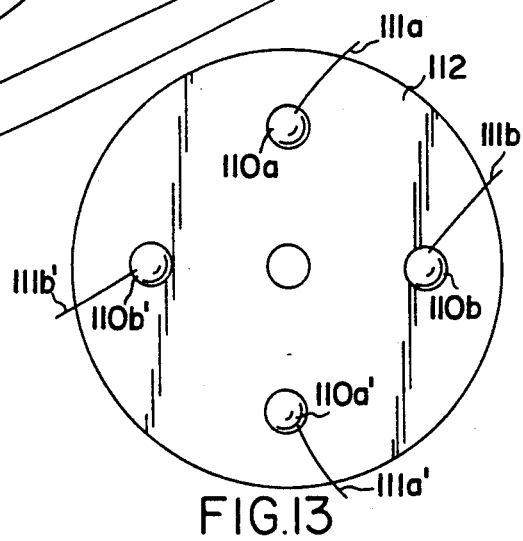
FIG. 13 is a front plan view of the non-conductive polymeric disc used in the switch of FIG. 12.

In FIGS. 7 and 8 conventional prior art two-pole interferential therapy electrode set-ups are illustrated. As noted earlier, the two-pole method permits a more specific selection of treatment location because the depth of modulation is 100% everywhere between the electrodes as shown in FIG. 7. Since the modulated current is occurring even in cutaneous tissue, the current intensity is less than that for a prior art four-pole method since skin irritations may occur. In addition, in a two-pole method, the area of coverage is limited as shown in field pattern or interference field 21 of FIG. 7. In FIG. 7 electrodes 22 and 23 are spaced as in conventional two-pole methods. The amplitude of the modulated current is diminished in areas that are not directly between the electrodes 22 and 23. A clinician may attempt to solve this problem by increasing the size of the electrodes 24 and 25 as shown in FIG. 8 but as the edges of the two electrodes 24 and 25 get closer together, the path of least electrical resistance becomes more superficial, see FIG. 8. The areas of coverage or field pattern 21 in FIG. 8 clearly show the space 26 between coverage 21 that is not affected. The switch is constructed as follows as shown in FIGS. 11 and 12. Input wires 101a, 101a', 101b, and 101b' (corresponding to wires 15 in FIG. 1) from a conventional interferential generator connect with brushes 102a, 102a', 102b, and 102b' respectively. Each brush couples to armatures 103a, 103a', 103b, and 103b', respectively, which are mounted on drive tube 104. Drive tube 104, made of an electrically non-conductive material, is driven by a variable speed motor 105 (powered by an appropriate source). Motor 105 is mounted to enclosure 106 by two stove bolts 107 and nuts 108 with compressed springs 109 to cause contact between $\frac{3}{8}$" ball bearing brushes 110a, 110a', 110b, and 110b'. Armatures 103a,103a', 103b, and 103b' are connected to ball bearing brushes 110a, 110a', 110b, and 110b', respectively, by electrically insulated wires 111a, 111a', 111b and 111b', respectively. Ball bearing brushes 110a, 110a', 110b, and 110b' are positioned into $\frac{1}{4}$" recessed holes positioned 90° apart relative to the axis of rotation into electrically non-conductive Teflon disk 112 which is mounted with a thermal weld to drive tube 104. Five copper wedges 113a, 113b, 113c, 113d, and 113e (72° arc each) are mounted onto electrically non-conductive disk 114 with 0.1" space between adjacent wedges. Disk 114 is mounted by two angle brackets 115 and bolts 107 and nuts 108 to enclosure 106. Copper wedges 113a, 113b, 113c, 113d, and 113e are soldered to electrically insulated output wires 115a, 115b, 115c, 115d, and 115e which feed output electrodes 116a, 116b, 116c, 116d, and 116e which are placed on patient 117 about the perimeter of the targeted treatment area in consecutive order (i.e. 116a next to 116b which is next to 116c which is next to 116d which is next to 116e which is next to 116a). Although this gives a specific layout for a switch (i.e. four-pole input and five-electrode output using a motor-driven mechanical switch) the nature of this switching concept to cause the interferential pattern to progress over time can be incorporated into crystal timed integrated circuits with non-mechanical switching. And the output is not limited to three or five output electrodes. For example, if an even number of output electrodes were used (i.e. six) this technique could be used paravertebrally to treat multiple spinal level lesions.

The preferred and optimumly preferred embodiments of the present invention have been described herein and shown in the accompanying drawing to illustrate the underlying principles of the invention but it is to be understood that numerous modifications and ramifications may be made without departing from the spirit and scope of this invention.

What is claimed is:

1. A method for treating a patient by utilizing interferential electrical stimulation which comprises positioning a plurality of electrodes on said patient's body, said plurality of electrodes comprising initially at least two active electrodes and at least one additional inactive electrode, said plurality of electrodes positioned at an area of said patient's body adjacent a targeted area to be treated, inducing an electrical interference pattern each having an initial axis of orientation, said initial axis provided by activation of all of said active electrodes, said at least one additional inactive electrode being positioned on said patient's body at a location adjacent said at least two electrodes, providing means for said plurality of electrodes to induct interferential electrical tissue stimulation, providing said plurality of electrodes with coupling means to a stimulation current to provide active electrodes and with uncoupling means to all electrical stimulation sources to provide at least one inactive electrode, initiating a momentary coupling of said active electrodes and said at least one inactive electrode so that the coupling of said at least one inactive electrode with one active electrode behaves as a larger single electrode, causing the axis of the electrical interference pattern of said active electrode to shift to an axis between said active and inactive electrodes, rotatably shifting said orientation of the electrical interference patterns over a given time to provide means for continuously shifting said axis of each electrical interference pattern over an expanded area of said patient's body when compared to an area of said body affected by said initial electrical interference patterns.

2. The method of claim 1 wherein said plurality of electrodes comprises two electrodes and as said at least one additional electrode, a third electrode adjacent said two electrodes.

3. The method of claim 1 wherein said plurality of electrodes comprises four electrodes and as said at least one additional electrode, a fifth electrode positioned therebetween.

4. An interferential electrotherapeutic device for use in electrical stimulation which comprises in combination a source of electrical power, a switching means and a plurality of electrodes, said plurality of electrodes comprising initially at least two separated active electrodes and at least one additional inactive electrode positioned at any point adjacent said active electrodes, each of said active electrodes having means upon activation to induce an interference pattern having an initial axis of orientation, means to induce interferential electrical tissue stimulation, means to cause a momentary coupling of one of said active electrodes and said at least one inactive electrode so they behave as a larger single electrode, switching means to cause the axis of the electrical interference pattern of said active electrode to shift to an axis between said active and inactive electrodes, said switching means being in electrical contact with said electrodes and having means to continuously shift said axis of each electrical interference pattern of each electrode and deliver carrier currents over an expanded area when compared to said electrodes without electrical connection to said switching means.

5. The device of claim 4 wherein said plurality of electrodes comprises two electrodes having as said additional electrode a third electrode adjacent said two electrodes.

6. The device of claim 4 wherein said plurality of electrodes comprises three separated electrodes having as said additional electrode a fourth electrode at a location somewhere adjacent said three electrodes.

7. The device of claim 4 wherein said plurality of electrodes comprises at least five electrodes separated from each other, and an additional electrode positioned somewhere adjacent of said at least five electrodes.

* * * * *